United States Patent [19]
Voigt et al.

[11] Patent Number: 5,537,534
[45] Date of Patent: Jul. 16, 1996

[54] DISK ARRAY HAVING REDUNDANT STORAGE AND METHODS FOR INCREMENTALLY GENERATING REDUNDANCY AS DATA IS WRITTEN TO THE DISK ARRAY

[75] Inventors: Douglas L. Voigt; Marvin D. Nelson, both of Boise, Id.

[73] Assignee: Hewlett-Packard Company, Palo Alto, Calif.

[21] Appl. No.: 386,582

[22] Filed: Feb. 10, 1995

[51] Int. Cl.[6] ................................................. G06F 11/00
[52] U.S. Cl. .................................. 395/182.04; 395/441
[58] Field of Search .......................... 395/182.04, 441, 395/440, 182.05, 185.05; 371/40.1, 51.1

[56] References Cited

U.S. PATENT DOCUMENTS

| | | | |
|---|---|---|---|
| 4,092,732 | 5/1978 | Ouchi | 364/900 |
| 4,914,656 | 4/1990 | Dunphy, Jr. et al. | 395/182.05 |
| 4,989,205 | 1/1991 | Dunphy, Jr. et al. | 395/182.04 |
| 5,072,378 | 12/1991 | Manka | 395/182.04 |
| 5,124,987 | 6/1992 | Milligan et al. | 395/182.04 |
| 5,155,835 | 10/1992 | Belsan et al. | 395/182.04 |
| 5,155,845 | 10/1992 | Beal et al. | 395/182.04 |
| 5,195,100 | 3/1993 | Katz et al. | 371/66 |
| 5,237,658 | 8/1993 | Walker et al. | 395/200 |
| 5,278,838 | 1/1994 | Ng et al. | 371/10.1 |
| 5,287,462 | 2/1994 | Jibbe et al. | 395/275 |
| 5,289,418 | 2/1994 | Youngerth | 365/201 |
| 5,297,258 | 3/1994 | Hale et al. | 395/275 |
| 5,333,305 | 7/1994 | Neufeld | 395/182.04 |
| 5,375,128 | 12/1994 | Menon et al. | 395/182.04 |
| 5,392,244 | 2/1995 | Jacobson et al. | 371/21.1 |
| 5,408,644 | 4/1995 | Schneider et al. | 395/182.04 |
| 5,410,667 | 4/1995 | Belsan et al. | 395/425 |

OTHER PUBLICATIONS

Triantafillou et al., "Supporting Partial Data Accesses To Replicated Data" IEEE pp. 32–42, 1994.
Mogi et al, "Dynamic Parity Stripe Reorganizations Fro Raid5 Disk Arrays", 1994 Parallel and Dist. Info. Sys. Conf., IEEE, pp. 17–26.

Primary Examiner—Robert W. Beausoliel, Jr.
Assistant Examiner—Joseph E. Palys

[57] ABSTRACT

A data storage system has a disk array having multiple storage disks and a disk array controller coupled to the disk array to coordinate data transfer to and from the storage disks. The disk array is configured into multiple stripes where each stripe extends across multiple ones of the storage disks. Additionally, each stripe consists of multiple segments of storage space where each segment is a portion of the stripe that resides on a single storage disk in the disk array. A memory manager is provided to manage memory allocation for storing user data redundantly according to parity redundancy techniques. The memory manager maintains a partial stripe pointer to reference individual stripes in the disk array and a segment fill pointer to references individual segments in the referenced stripe. These pointers are used to select a non-filled stripe and individual segments in that stripe. The memory manager writes user data to a selected segment and incrementally determines a parity value for the stripe after each segment is written. The parity value is based upon the user data contained in those segments of the stripe that have been written. The empty segments in the stripe are not managed during the write process and thus are not included in the incremental parity generation.

21 Claims, 7 Drawing Sheets

DISKS

| 0 | 1 | 2 | 3 | STRIPE NUMBER |
|---|---|---|---|---|
| 0 | 0' | 1 | 1' | 0 |
| 2 | 2' | 3 | 3' | 1 |
| 4 | 4' | 5 | 5' | 2 |
| 6 | 6' | 7 | 7' | 3 |
| * | * | * | * | * |
| * | * | * | * | * |
| * | * | * | * | * |
| T−1 | T−1' | T | T' | S |

*Fig 2*

DISKS

| 0 | 1 | 2 | 3 | STRIPE NUMBER |
|---|---|---|---|---|
| 0 | 1 | 2 | P | 0 |
| 3 | 4 | P | 5 | 1 |
| 6 | P | 7 | 8 | 2 |
| P | 9 | 10 | 11 | 3 |
| * | * | * | * | * |
| * | * | * | * | * |
| * | * | * | * | * |
| P | R−2 | R−1 | R | Q |

*Fig 3*

DISK ARRAY HAVING REDUNDANT STORAGE AND METHODS FOR INCREMENTALLY GENERATING REDUNDANCY AS DATA IS WRITTEN TO THE DISK ARRAY

FIELD OF THE INVENTION

This invention relates to disk arrays, and more particularly, to redundant hierarchic disk array data storage systems having redundant storage capabilities. This invention also relates to methods for incrementally generating redundancy as data is written to the disk array.

BACKGROUND OF THE INVENTION

Disk array data storage systems have multiple storage disk drive devices which are arranged and coordinated to form a single mass storage system. There are three primary design criteria for such storage systems: cost, performance, and availability. It is most desirable to produce memory devices that have a low cost per megabyte, a high input/output performance, and high data availability. "Availability" is the ability to access data stored in the storage system and the ability to insure continued operation in the event of some failure. Typically, data availability is provided through the use of redundancy wherein data, or relationships among data, are stored in multiple locations. In the event that a storage disk in the disk array partially or completely fails, the user data can be reconstructed via the redundant data stored on the remaining disks.

There are two common methods of storing redundant data. According to the first or "mirror" method, data is duplicated and stored in two separate areas of the storage system. For example, in a disk array, the identical data is provided on two separate disks in the disk array. The mirror method has the advantages of high performance and high data availability due to the duplex storing technique. However, the mirror method is also relatively expensive as it effectively doubles the cost of storing data.

In the second or "parity" method, a portion of the storage area is used to store redundant data, but the size of the redundant storage area is less than the remaining storage space used to store the original data. For example, in a disk array having five disks, four disks might be used to store data with the fifth disk being dedicated to storing redundant data. The parity method is advantageous because it is less costly than the mirror method, but it also has lower performance and availability characteristics in comparison to the mirror method.

This invention is particularly directed toward storing data according to parity techniques. In conventional disk arrays, the space on the storage disks are configured into multiple stripes where each stripe extends across the storage disks. Each stripe consists of multiple segments of storage space, where each segment is a portion of the stripe that resides on a single storage disk in the disk array.

During initialization of a prior art disk array, the storage disks are formatted and the parity for each stripe is set. After initialization, four I/O accesses are required to write data to the disk array: a first I/O to read the data to be updated from a selected stripe, a second I/O to read the corresponding parity for data in that stripe, a third I/O to write new data back to the stripe, and a fourth I/O to write a new parity that accounts for the new data back to the stripe. It would be desirable to reduce the number of I/Os required to write data to stripes in disk arrays.

One technique that has been used in some prior art disk arrays is to cache the parity values. This reduces the need to read the parity from the disk array during each write process, thereby reducing the number of I/Os to three. However, there remains a need to further reduce the number of I/Os required to write data to stripes in the disk array.

SUMMARY OF THE INVENTION

This invention provides a disk array data storage system having an improved write performance during parity writes that requires fewer I/Os. The disk array writes data to individual segments in a stripe, preferably in a sequential manner one segment at a time. A memory manager is provided which knows the sizes of the stripes, and the parity status of each segment in the stripes as to whether the segment contains data that is part of the parity value for the associated stripe.

In the preferred implementation, the memory manager tracks parity status of each segment through the use of two types of pointers: one or more partial stripe pointers that keep track Of stripes that are being filled, and one or more segment fill pointers that reference specific segments in the stripes that are being filled. With respect to a selected stripe, segments in front of the segment fill pointer are known to contain data that is incorporated into the stripe parity and segments following the segment fill pointer are empty and not yet incorporated into the stripe parity. With respect to stripes not referenced by the partial stripe pointer, stripes that contain data are considered to have all data segments represented by the stripe parity and all empty stripes are understood not to contain data or have any parity value representing those segments.

Once a stripe is selected, data is written to the segment referenced by the segment fill pointer. During this data write, a parity value corresponding to the data contained in all filled segments in the selected stripe is incrementally generated and cached in a separate non-volatile memory, such as an NVRAM. The empty segments in the stripe are not managed during the write process and thus are not included in the incremental parity generation. After all data segments in the stripe are filled, the final parity value is written to the parity segment in the stripe. The process can then be repeated for the next unfilled or partially filled stripe.

A disk array implemented with sequential segment writing, incremental parity generation, and parity caching according to this invention eliminates the prior art I/Os of reading the old data and reading the old parity. Additionally, it can reduce the number of times that a parity value is written to the disk array to a single write after the entire stripe is filled. This results in a significant improvement in write performance.

DESCRIPTION OF THE DRAWINGS

Preferred embodiments of the invention are described below with reference to the following accompanying drawings depicting examples embodying the best mode for practicing the invention.

FIG. 2 is a diagrammatic illustration of storage space on multiple storage disks and shows data storage according RAID Level 1.

FIG. 3 is a diagrammatic illustration of storage space on multiple storage disks and shows data storage according RAID Level 5.

DETAILED DESCRIPTION OF THE INVENTION

This disclosure of the invention is submitted in furtherance of the constitutional purposes of the U.S. Patent Laws "to promote the progress of science and useful arts". U.S. Constitution, Article 1, Section 8.

Figure 1:
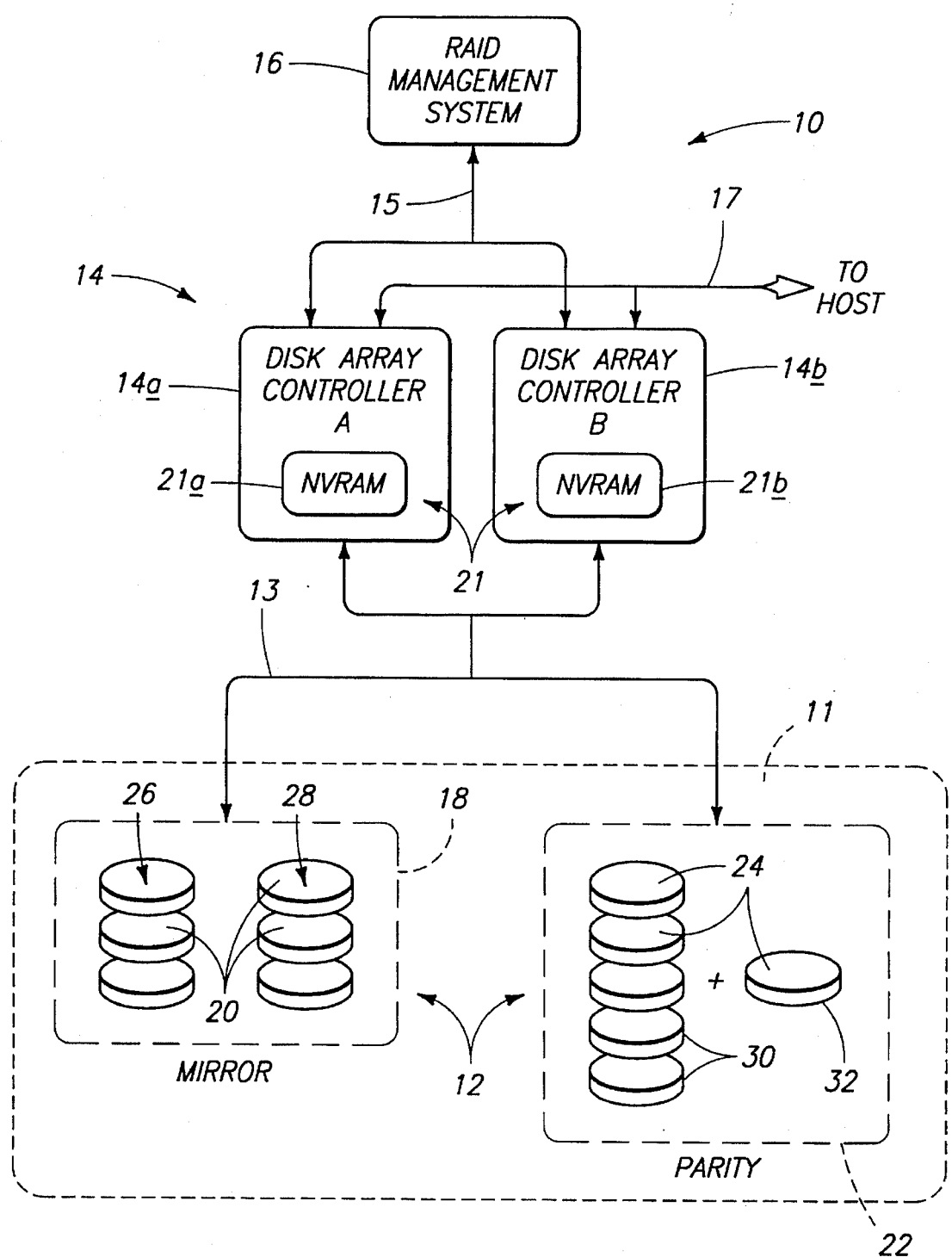
FIG. 1 is a diagrammatic block diagram of a disk array data storage system according to this invention.

FIG. 1 shows a data storage system 10 constructed according to this invention. Preferably, data storage system 10 is a disk array data storage system which includes a hierarchic disk array 11 having a plurality of storage disks 12, a disk array controller 14 coupled to the disk array 11 to coordinate transfer of user data to and from the storage disks 12, and a RAID management system 16. This invention is described in the context of its preferred implementation as a redundant hierarchic disk array system. It is noted, however, that aspects and concepts of this invention can be utilized in other types of disk array data storage systems, such as non-hierarchic redundant disk arrays.

For purposes of this disclosure, a "disk" is any non-volatile, randomly accessible, rewritable mass storage device which has the ability of detecting its own storage failures. It includes both rotating magnetic and optical disks and solid-state disks, or non-volatile electronic storage elements (such as PROMs, EPROMs, and EEPROMs). The term "disk array" is a collection of disks, the hardware required to connect them to one or more host computers, and management software used to control the operation of the physical disks and present them as one or more virtual disks to the host operating environment. A "virtual disk" is an abstract entity realized in the disk array by the management software.

The term "RAID" (Redundant Array of Independent Disks) means a disk array in which part of the physical storage capacity is used to store redundant information about user data stored on the remainder of the storage capacity. The redundant information enables regeneration of user data in the event that one of the array's member disks or the access path to it fails. A more detailed discussion of RAID systems is found in a book entitled, *The RAIDBook: A Source Book for RAID Technology*, published Jun. 9, 1993, by the RAID Advisory Board, Lino Lakes, Minn.

Disk array controller 14 is coupled to disk array 11 via one or more interface buses 13, such as a small computer system interface (SCSI). RAID management system 16 is operatively coupled to disk array controller 14 via an interface protocol 15. Data memory system 10 is also coupled to a host computer (not shown) via an I/O interface bus 17. RAID management system 16 can be embodied as a separate component, or configured within disk array controller 14 or within the host computer to provide a data manager means for controlling disk storage and reliability levels, and for transferring data among various reliability storage levels.

These reliability storage levels are preferably mirror or parity redundancy levels as described below, but can also include a reliability storage level with no redundancy at all.

The disk array controller 14 is preferably implemented as a dual controller consisting of disk array controller A, referenced by numeral 14a, and disk array controller B, referenced by numeral 14b. Dual controllers 14a and 14b enhance reliability by providing continuous backup and redundancy in the event that one controller becomes inoperable. This invention can be practiced, however, with a single controller or other architectures.

The hierarchic disk array 11 can be characterized as different storage spaces, including its physical storage space and one or more virtual storage spaces. These various views of storage are related through mapping techniques. For example, the physical storage space of the disk array can be mapped into a virtual storage space which delineates storage areas according to the various data reliability levels. Some areas within the virtual storage space can be allocated for a first reliability storage level, such as mirror or RAID level 1, and other areas can be allocated for a second reliability storage level, such as parity or RAID level 5. The various mapping techniques and virtual spaces concerning RAID levels are described below in more detail.

Data storage system 10 includes a memory map store 21 that provides for persistent storage of the virtual mapping information used to map different storage spaces into one another. The memory map store is external to the disk array, and preferably resident in the disk array controller 14. The memory mapping information can be continually or periodically updated by the controller or RAID management system as the various mapping configurations among the different views change.

Preferably, the memory map store 21 is embodied as two non-volatile RAMs (Random Access Memory) 21a and 21b which are located in respective controllers 14a and 14b. An example non-volatile RAM (NVRAM) is a battery-backed RAM. A battery-backed RAM uses energy from an independent battery source to maintain the data in the memory for a period of time in the event of power loss to the data storage system 10. One preferred construction is a self-refreshing, battery-backed DRAM (Dynamic RAM).

The dual NVRAMs 21a and 21b provide for redundant storage of the memory mapping information. The virtual mapping information is duplicated and stored in both NVRAMs 21a and 21b according to mirror redundancy techniques. In this manner, NVRAM 21a can be dedicated to storing the original mapping information and NVRAM 21b can be dedicated to storing the redundant mapping information. In an alternative construction, a mirrored memory map store can be configured using a single non-volatile RAM with sufficient space to store the data in duplicate.

As shown in FIG. 1, disk array 11 has multiple storage disk drive devices 12. Example sizes of these storage disks are one to three Gigabytes. The storage disks can be independently connected or disconnected to mechanical bays that provide interfacing with SCSI bus 13. In one implementation, the data storage system is designed with twelve active mechanical bays. Four SCSI buses are used to interface these bays with disk array controller 14 (i.e., one bus per three mechanical bays). If the active bays are fully loaded, the data storage system has an example combined capacity of 12–36 Gigabytes. Disk array controller 14 recognizes storage disks 12 regardless into which bay they are plugged. The data storage system 10 is designed to permit "hot plug" of additional disks into available mechanical bays in the disk array while the disk array is in operation.

The storage disks 12 in disk array 11 can be conceptualized, for purposes of explanation, as being arranged in a mirror group 18 of multiple disks 20 and a parity group 22 of multiple disks 24. Mirror group 18 represents a first memory location or RAID area of the disk array which stores data according to a first or mirror redundancy level. This mirror redundancy level is also considered a RAID Level 1. RAID Level 1, or disk mirroring, offers the highest data reliability by providing one-to-one protection in that every bit of data is duplicated and stored within the data storage system. The mirror redundancy is diagrammatically represented by the three pairs of disks 20 in FIG. 1. Original data can be stored on a first set of disks 26 while duplicative, redundant data is stored on the paired second set of disks 28.

FIG. 2 illustrates the storage of data according to RAID Level 1 in more detail. The vertical columns represent individual disks, of which disks 0, 1, 2, and 3 are illustrated. The physical storage space contained in this disk array of four disks can be configured into multiple stripes, as represented by the horizontal rows. A "stripe" extends across the storage disks and is comprised of numerous, preferably equal sized segments of storage space where one segment is associated with each disk in the array. That is, a segment is the portion of a stripe that resides on a single disk. Each stripe holds a predetermined amount of data which is distributed across the storage disks. Some segments of a stripe are used for original data while other segments are used for redundant data.

In this example of mirror redundancy (RAID Level 1), data stored on disk 0 in segment 0 of stripe 0 is duplicated and stored on disk 1 in segment 0' of stripe 0. Similarly, data stored on disk 2 in segment 5 of stripe 2 is mirrored into segment 5' of stripe 2 on disk 3. In this manner, each piece of data is duplicated and stored on the disks. The redundancy layout of FIG. 2 is provided for explanation purposes. The redundant data need not be placed neatly in the same stripe as is shown. For example, data stored on disk 0 in segment 2 of stripe 1 could be duplicated and placed on disk 3 in segment T' of stripe S.

With reference again to FIG. 1, the parity group 22 of disks 24 represent a second memory location or RAID area in which data is stored according to a second redundancy level, such as RAID Level 5. In this explanatory illustration of six disks, original data is stored on the five disks 30 and redundant "parity" data is stored on the sixth disk 32.

FIG. 3 shows a parity RAID area layout in more detail. Similar to the mirror RAID area layout of FIG. 2, the physical storage space of disks 0, 1, 2, 3 can be configured into multiple equal sized stripes. In this illustrated example, data is stored according to RAID Level 5 and the redundant data stored in the segments is referenced by letter P. The redundant P segments store the parity of the other segments in the stripe. For example, in stripe 0, the redundant P segment on disk 3 stores the parity of disks 0, 1, and 2. The parity for each stripe is computed by some function, such as an exclusive OR function which is represented by the symbol "$\oplus$". The parities for the first four stripes (with the subscript numeral representing the corresponding stripe) are as follows:

$P_0$ = Segment 0 $\oplus$ Segment 1 $\oplus$ Segment 2
  = Disk 0 $\oplus$ Disk 1 $\oplus$ Disk 2

$P_1$ = Segment 3 $\oplus$ Segment 4 $\oplus$ Segment 5
  = Disk 0 $\oplus$ Disk 1 $\oplus$ Disk 3

$P_2$ = Segment 6 $\oplus$ Segment 7 $\oplus$ Segment 8
  = Disk 0 $\oplus$ Disk 2 $\oplus$ Disk 3

$P_3$ = Segment 9 $\oplus$ Segment 10 $\oplus$ Segment 11
  = Disk 1 $\oplus$ Disk 2 $\oplus$ Disk 3

Parity redundancy allows regeneration of data which becomes unavailable on one of the disks. For example, if the data in segment 5 becomes unavailable, its contents can be ascertained from segments 3 and 4 and the parity data in segment P. Parity storage is less expensive than mirror storage, but is also less reliable and has a lower performance.

The disk arrangement of FIG. 1 is provided for conceptual purposes. In practice, the disk array 11 would simply have a plurality of disks 12 which are capable of storing data according to mirror and parity redundancy. Among the available storage space provided by all disks 12, a portion of that storage space would be allocated for mirror redundancy and another portion would be allocated for parity redundancy. Preferably, disks 12 are configured to contain plural, equal sized storage regions (referenced as numeral 35 in FIG. 4), wherein individual regions have multiple segments. The regions are grouped together to form RAID areas in one virtual view of the storage space. Additionally, another (host-defined) view of storage space is presented to the user or host so that the RAID areas and data redundancy storing techniques are transparent to the user or host. These features are discussed below in more detail with reference to FIG. 4.

Data storage system 10 manages the "migration" of data between mirror and parity storage schemes. The management of both types of redundancy is coordinated by RAID management system 16 (FIG. 1). RAID management system 16 manages the two different types of RAID areas in the disk array as a memory hierarchy with the mirror RAID areas acting similar to a cache for the parity RAID areas. RAID management system 16 shifts, organizes, and otherwise manages the data between the mirror and parity RAID areas in accordance with a defined performance protocol. The process of moving data between the mirror and parity RAID areas is referred to as "migration".

Data storage system 10 tries to place the more performance-critical data in the mirror RAID areas since this affords the highest performance and reliability. The performance protocols implemented by RAID management system 16 includes one of two preferred migration policies. According to the first migration policy, known as "access frequency", the most frequently accessed data on the hierarchic disk array is maintained in the mirror RAID area 18. Less frequently accessed data is maintained in the parity RAID area 22. According to a second migration policy, known as "access recency", the most recently accessed data is maintained in the mirror RAID area 18 while the less recently accessed data is stored in parity RAID area 22. Other performance protocols may be employed. Ideally, such protocols are defined based upon the specific computer application and the needs of the user.

Additionally, the RAID management system 16 automatically "tunes" the storage resources of a data storage system according to a function of two parameters: size of the physical storage capacity and size of the present amount of user data being stored in the data storage system. Initially, all data is stored in mirror RAID areas because this affords the highest performance and reliability. As more data is added to the data storage system, the data is migrated between mirror RAID areas and parity RAID areas to optimize performance and reliability. As the data storage system approaches full capacity, more and more data is migrated to parity RAID areas in an effort to meet all demands by the user while still providing reliability through redundancy. Accordingly, the data storage system of this invention affords maximum flexibility and adaptation. It does not require the user to select a specific storage regime, but instead can adapt to any demand placed on it by the user.

Figure 4:
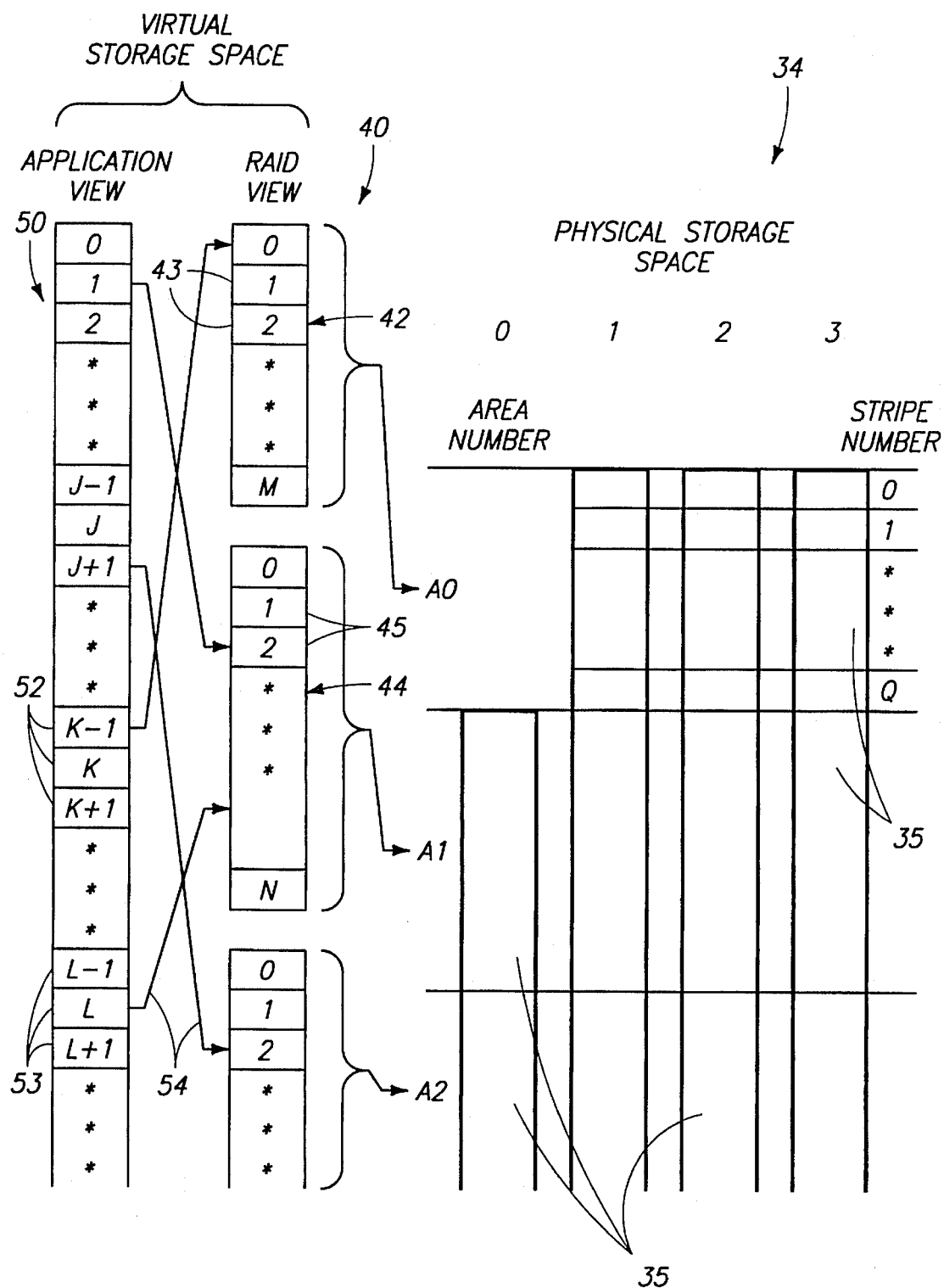
FIG. 4 is a diagrammatic illustration of a memory mapping arrangement of this invention where two virtual storage spaces are mapped onto a physical storage space.

FIG. 4 illustrates a memory mapping of the available storage space of data storage system 10 as multiple tiers of mapped virtual storage space. Each vertically elongated rectangle in the diagram represents a view of the physical storage space. In this diagram, physical storage space 34 is referenced by two virtual storage views 40 and 50. Physical storage space 34 is represented by four disks (such as disks 12 in FIG. 1) referenced by numerals 0, 1, 2, and 3. The four rectangles associated with the disks represent a view of the physical storage space wherein disks 1, 2, and 3 have approximately equal storage capacity, and disk 0 has slightly less storage capacity. Example storage capacities for such disks are 1–3 Gigabytes. The storage space 34 is partitioned into areas A0, A1, A2, etc. Individual areas contain numerous stripes, such as stripes O–Q in area A0. Individual areas also contain numerous regions 35. Regions 35 preferably consist of a selected number of uniform sized segments on every storage disk so that the regions are equal in size across the entire disk array. An example size of one region 35 is one Megabyte.

The storage space of the disks are mapped into a first, intermediate, RAID-level virtual view 40 of the physical storage space 34. This first virtual view is conceptually a set of RAID areas which can be mapped to a second application view that represents a contiguously addressable storage space. The physical configuration and RAID views of the storage space are hidden from the application view.

The RAID area storage space 40 is the view of storage that identifies the mirror and parity storage space. For instance, a RAID area 42 may represent a mirror RAID area of M allocation blocks 43 while RAID area 44 may represent a parity RAID area of N allocation blocks 45. The allocation blocks 43 and 45 are preferably equal sized, with an example size being 64 Kilobytes. These RAID areas relate to corresponding physical areas A0, A1, A2, etc., on the physical storage space 34. As an example, sixteen 64K allocation blocks 43 or 45 at the RAID virtual view can be mapped onto a single 1M region 35.

The mirror and parity RAID areas may or may not consume the entire storage space 34 of the disk array. Accordingly, during certain applications, there may be unused and undesignated storage space that does not correspond to a particular RAID area. However, such storage space can be converted into a mirror or parity RAID area. It is also noted that the RAID areas are shown as being mapped into contiguous areas on the disk array, where each region associated with a RAID area is located at the same physical address on each storage disk. The RAID areas may alternatively be mapped into noncontiguous areas on the disk array as well.

The storage space available in the RAID areas is mapped into a second, front end, application-level virtual view 50 which is a view of storage as defined by and presented to the user or host application program. When viewed by the user or host application program, the application-level virtual view 50 can represent a single large storage capacity indicative of the available storage space on storage disks 12. Virtual storage space 50 presents a view of a linear set of equal sized storage virtual blocks 52 and 53, referenced individually as 0, 1, 2, . . . J–1, J, J+1, . . . , L–1, L, L+1, . . . , etc. Virtual blocks 52 and 53 are preferably the same size as the allocation blocks in RAID area 40, with an example size being 64 Kilobytes. The virtual block storage space 50 is represented by a table of references or pointers (as represented by arrows 54) to allocation blocks in the view presented by RAID areas 40. Virtual blocks 52 and 53 at the application virtual view 50 are therefore associated with allocation blocks 43 and 45 at the RAID virtual view 40 via the pointers maintained in the virtual block table. There are at least two types of RAID areas that can be referenced from the virtual block table: mirror and parity.

The RAID management system 16 can dynamically alter the configuration of the RAID areas over the physical storage space. The number of RAID areas for each type may be increased or decreased depending upon the amount of user data being stored in the system and the size of the physical disk storage space. As a result, the mapping of the RAID areas in the RAID-level virtual view 40 onto the disks and the mapping of the application-level virtual view 50 to RAID view 40 are generally in a state of change. The memory map store in NVRAMs 21a and 21b (FIG. 1) maintains the current mapping information used by RAID management system 16 to map the RAID areas onto the disks, as well as the information employed to map between the two virtual views. As the RAID management system dynamically alters the RAID level mappings, it also updates the mapping information in the memory map store to reflect the alterations.

The migration operation of memory system 10 will now be described with reference to FIGS. 1 and 4.

For purposes of continuing explanation, virtual blocks 53 of the application-level virtual storage space 50 reference associated allocation blocks 45 in parity RAID area 44 stored in area A1 of physical storage space 34. Such virtual blocks 53 may be referred to as "parity virtual blocks" while the associated allocation blocks 45 are referred to as "parity allocation blocks". Similarly, virtual blocks 52 reference associated allocation blocks 43 in mirror RAID area 42 stored in area A0 of physical storage space 34. Such virtual blocks 52 may be referred to herein as "mirror virtual blocks" while the associated allocation blocks 43 are referred to as "mirror allocation blocks".

In general, to migrate data from one RAID area to another, a virtual block associated with an allocation block of a first RAID level type (such as mirror or Level 1) is selected. Then, an unused allocation block representing a second RAID level type (such as parity or Level 5) is located. If an unused allocation block cannot be located, one is created. Data is next transferred from the allocation block previously associated with the selected virtual block to the unused allocation block which causes the data to undergo a redundancy level change. For example, data once stored according to mirror redundancy would now be stored according to parity redundancy, or vice versa. As a final step, the mapping 54 of the application-level virtual storage space 50 to the RAID-level virtual storage space 40 is modified and updated to reflect the shift of data. The selected virtual block that was formerly associated with an allocation block of the first RAID level type now references via an updated pointer an allocation block of the second RAID level type which contains the migrated data. Any mapping change occurring during this transaction would be updated in memory map store 21.

The continuing discussion provides a more detailed explanation of migrating data between mirror and parity storage areas according to preferred methods and sequences of this invention. To migrate data from parity to mirror storage, the following sequence is employed:

1. The RAID management system locates an unused mirror allocation block 43 in a mirror RAID area 42.
2. If none can be found, the RAID management system creates a mirror allocation block (discussed below).
3. The RAID management system suspends new storage requests to the virtual block to be migrated.
4. The RAID management system waits until all active data storage requests to the virtual block are completed.
5. The data from the parity allocation block 45 associated with virtual block 53 is read into a temporary memory buffer.
6. The data is then written to the mirror allocation block 43 chosen in step 2.
7. The virtual block table is modified to reference the new location of the data in the mirror allocation block 43.
8. The suspended storage requests are resumed.

According to the above procedure, a virtual block 53 in the application-level virtual view 50 migrated from parity to mirror storage. Relative to the intermediate virtual view 40, data has migrated from a parity allocation block 45 in parity RAID area 44 to a mirror allocation block 43 in mirror RAID area 42. In the physical storage space data has moved from area A1 to area A0.

If an unused mirror allocation block cannot be located (step 1 above), the RAID management system tries the following preferred sequence of three techniques. First, the RAID management system will try to locate an unused (and thus undesignated) RAID area, which can be converted to a mirror RAID area without violating the system threshold of unused RAID-level storage that is needed to guarantee that migration can always proceed. If this fails and the system has more than the reserved amount of unused RAID-level storage, the system migrates data within parity storage to collect unused parity allocation blocks into unused RAID areas. If this migration yields an unused RAID area that can be converted to a mirror RAID area as above, then the system converts it to a mirror RAID area. Otherwise, the system alternately migrates data from mirror to parity storage, packs mirror storage, and converts unused RAID-level storage to parity until the system increases unused RAID-level storage sufficiently for the location of an unused mirror allocation block or a conversion of an unused RAID area to a mirror RAID area. Since mirror allocation blocks occupy more physical storage space than parity allocation blocks, this last technique will result in a net increase in the amount of unused RAID-level storage.

The creation/conversion protocol used to locate and establish unused mirror allocation blocks is advantageous because it permits the RAID management system to selectively adjust the memory allocation between parity and mirror areas according to the amount of user data and the size of physical storage space. As data usage and storage capacity vary, the RAID management system employs one or more of the above three techniques to maximize the amount of data held in mirror storage.

The RAID management system attempts to avoid the situation in which a storage request must wait for the space-making sequence to yield an unused mirror allocation block by creating unused RAID areas during idle time. However, in some situations, storage requests may be suspended during the space-making sequence. The RAID management system configures the virtual block storage space in such a way that the virtual space will be smaller than the RAID view. This ensures that a free space equal to at least one RAID area is set aside for migration or other purposes. In this manner, the sequence of techniques will always yield an unused mirror allocation block.

To migrate data from mirror to parity storage, the following sequence is employed:

1. The RAID management system chooses a virtual block from 52 to migrate from mirror to parity storage according to a migration policy such as access recency or access frequency.
2. The RAID management system locates an unused parity allocation block 45 in a parity RAID area 44.
3. If such a block cannot be found, space reserved for migration is converted to a parity RAID area according to the above described creation techniques.
4. New storage requests to the virtual block to be migrated are suspended.
5. The RAID management system waits until all active storage requests to the virtual block are completed.
6. Data is read from the mirror allocation block 43 associated with virtual block 52 into a temporary memory buffer.
7. The data is written to the chosen parity allocation block 45.
8. The virtual block table is modified to reference the new location of the data in parity allocation block 45.
9. Data requests to the virtual block are resumed. The above two enumerated sequences provide examples of how the memory system of this invention can operate to migrate data between two different levels of redundancy.

While the above discussion focused on data migration between mirror and parity storage, this invention is particularly directed toward the process of writing data to the storage disks according to parity techniques. The storage management technique described above allows this invention to manage activity of the parity RAID areas in segment size pieces, thus enabling incremental parity generation.

As mentioned in the Background of the Invention section, conventional disk arrays write a default pattern, typically consisting of a repeating bit or byte pattern. An example pattern is to write all "1"s to the disk array. Conventional disk arrays also set the parity for each stripe therein during initialization procedures.

After this initialization process, the conventional disk array is ready to write user data. As used in this disclosure, "user data" means data bytes containing information pursuant to the application of the computing system. For instance, user data might consist of the data that is obtained from the host computer as a result of an application. User data might also consist of data recovered from the storage disk that had previously been the result of a computing application. "User data" is not intended to cover simple format patterns employed during initialization, such as a pattern of all "1"s.

In conventional disk arrays, four I/O accesses are required to write user data to the disk array: a first I/O to read the data to be updated from a selected stripe, a second I/O to read the corresponding parity for data in that stripe, a third I/O to write new data back to the stripe, and a fourth I/O to write a new parity that accounts for the new data back to the stripe.

According to the disk array of this invention, a memory manager sequentially writes user data to the stripe, one segment at a time, and incrementally generates a parity value during each data write. The memory manager caches the parity value until a parity for the entire stripe can computed. This final parity value is thereafter written to the stripe. The disk array significantly reduces the number of I/Os during a write procedure.

The memory manager includes a means for determining which data segments are incorporated into a stripe parity and which are not. That is, the memory manager knows the sizes of the stripes, as well as the parity status of each segment in the stripes with regard to whether the individual segment contains data that is part of the parity value for the associated stripe. In the preferred implementation, the memory manager tracks parity status of each segment through the use of two types of pointers: one or more partial stripe pointers which keep track of stripes that are being filled, and one or more segment fill pointers that reference specific segments in the stripes that are being filled. These pointers are preferably kept in a non-volatile memory for ready use by the memory manager.

Figure 5:
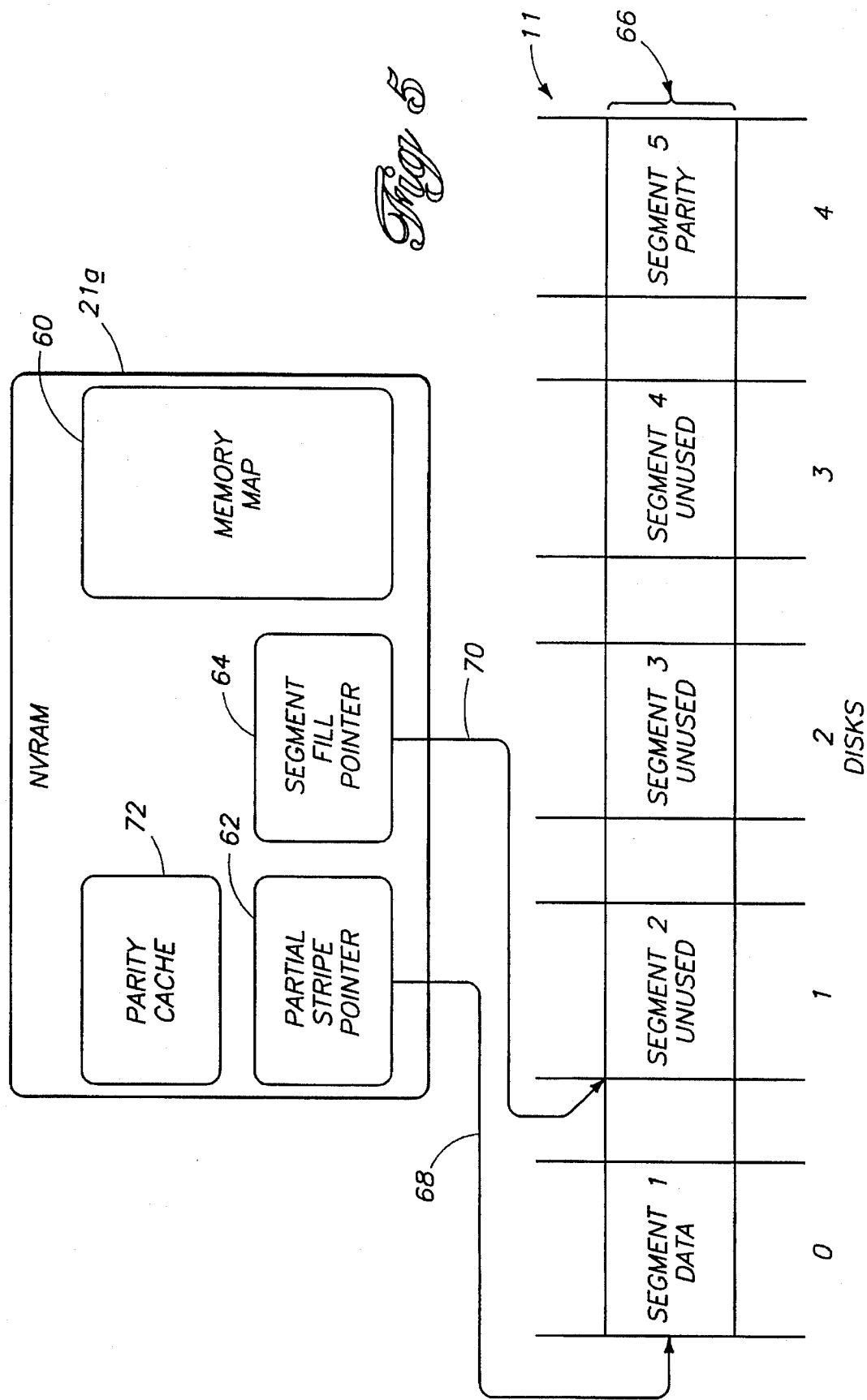
FIG. 5 is a diagrammatic block diagram illustrating the interaction between pointers maintained in a non-volatile memory and storage space on the disk array.

FIG. 5 shows NVRAM 21a containing a partial stripe pointer 62 and a segment fill pointer 64. In the illustrated example, the pointers are used to reference segments within stripe 66 that extends across disks 0–4 of disk array 11. NVRAM 21a also contains memory map 60 which tracks the mapping of the RAID-level and application-level virtual storage spaces. The mirror NVRAM 21b is not shown in this figure, but would contain identical information as illustrated in NVRAM 21a.

Partial stripe pointer 62 references individual stripes, and more particularly non-filled stripes, in the disk array. Initially, the partial stripe pointer identifies an empty stripe that contains no user data. Segment fill pointer 64 references individual segments within the stripe selected by partial stripe pointer 62. The segment fill pointer 64 locates the empty segment that is ready to be filled with user data. In FIG. 5, partial stripe pointer 62 references a non-filled stripe 66 as represented by arrow 68 and segment fill pointer 64 references segment 2 (as represented by arrow 70), the next empty segment in stripe 66. Preferably, the segment fill pointer sequentially steps through the stripe to reference each empty segment in a contiguous manner, beginning with segment 1 and ending with segment 5.

According to this preferred implementation, the memory manager effectively tracks the parity status of all segments in the disk array through the help of these two pointers. With respect to the stripe selected by partial stripe pointer 62, segments in front of segment fill pointer 64 are known to contain data that is incorporated into the stripe parity and segments following the segment fill pointer are known to be empty and not yet incorporated into the stripe parity. With respect to those stripes that are not referenced by partial stripe pointer 64, the stripes that contain data are considered to have all data segments represented by the stripe parity. The empty stripes are understood to contain no data or have any parity value representing those segments.

Once an empty stripe is identified by the partial stripe pointer, user data is written to the segment referenced by the segment fill pointer. In FIG. 5, user data has already been written to the first segment 1 in stripe 66. As the segment fill pointer 64 sequences through the remaining segments, user data is written to each segment in the stripe except the segment that is reserved for parity. In this case, parity is written to the last segment 5. If the parity segment is not the last one in the stripe, however, the segment fill pointer skips over the parity segment during its sequential pass through the stripe and then returns to write the parity to the parity segment after the user data has been placed in all data segments of the stripe. The position of the parity segment in the stripe is determined by a parity placement method which is common in the art. It is noted that user data is written only to the segment referenced by pointer 64, and the other data segments are left alone until they are referenced.

According to an aspect of this invention, a parity value is incrementally generated following each data write to a segment in the stripe. As described above with respect to FIG. 3, a parity value is computed according to a logical function, such as an exclusive or (XOR) function. When only one segment is filled, as shown in FIG. 5, the parity value is identical to the user data. As more segments fill, however, the parity value incrementally changes to reflect the parity for the user data that is contained in all filled segments. The empty or unused segments in the stripe are not managed during sequential write process and thus are not included in the incremental parity generation.

NVRAM 21a includes a parity cache 72 which temporarily stores the incremental parity value. As a new segment is written to, the memory manager computes a new parity value based on the logical function (i.e., XOR) of the previously cached parity value and the user data just written to the next segment. The sequential segment writing and incremental caching is repeated segment by segment until all data-bearing segments are filled.

As a result of the parity caching, the parity value need not be written to the disk array after each write. Instead, the parity value is only written to the disk array after all data segments have been filled. That is, when the segment fill pointer 64 reaches last segment 5, the RAID management system writes the parity value to the parity segment for stripe 66, which in this case is segment 5 although any segment within the stripe can be used to store parity.

The disk array of this invention eliminates the need to read user data and parity from the disk array during a write process, thereby eliminating the first two I/Os of conventional disk arrays. Additionally, by caching the parity value, the disk array effectively reduces the number of times that parity is written to the disk for each stripe. More specifically, whereas prior art disk arrays required four I/Os to write user data with parity, the disk array of this invention requires only $1+1/(N-1)$ I/Os to write user data with parity (where N equals the number of disks in the stripe).

As noted above, the partial stripe pointers 62, segment fill pointers 64, and parity cache 72 are managed and maintained by the memory manager. In the preferred implementation, the memory manager is embodied as the RAID management system 16 (FIG. 1) which also keeps track of the user data, redundant data, and unused space on the disk array. However, a memory manager configured solely to manage memory allocation according to parity storage can be used in the context of this invention.

Figure 6:
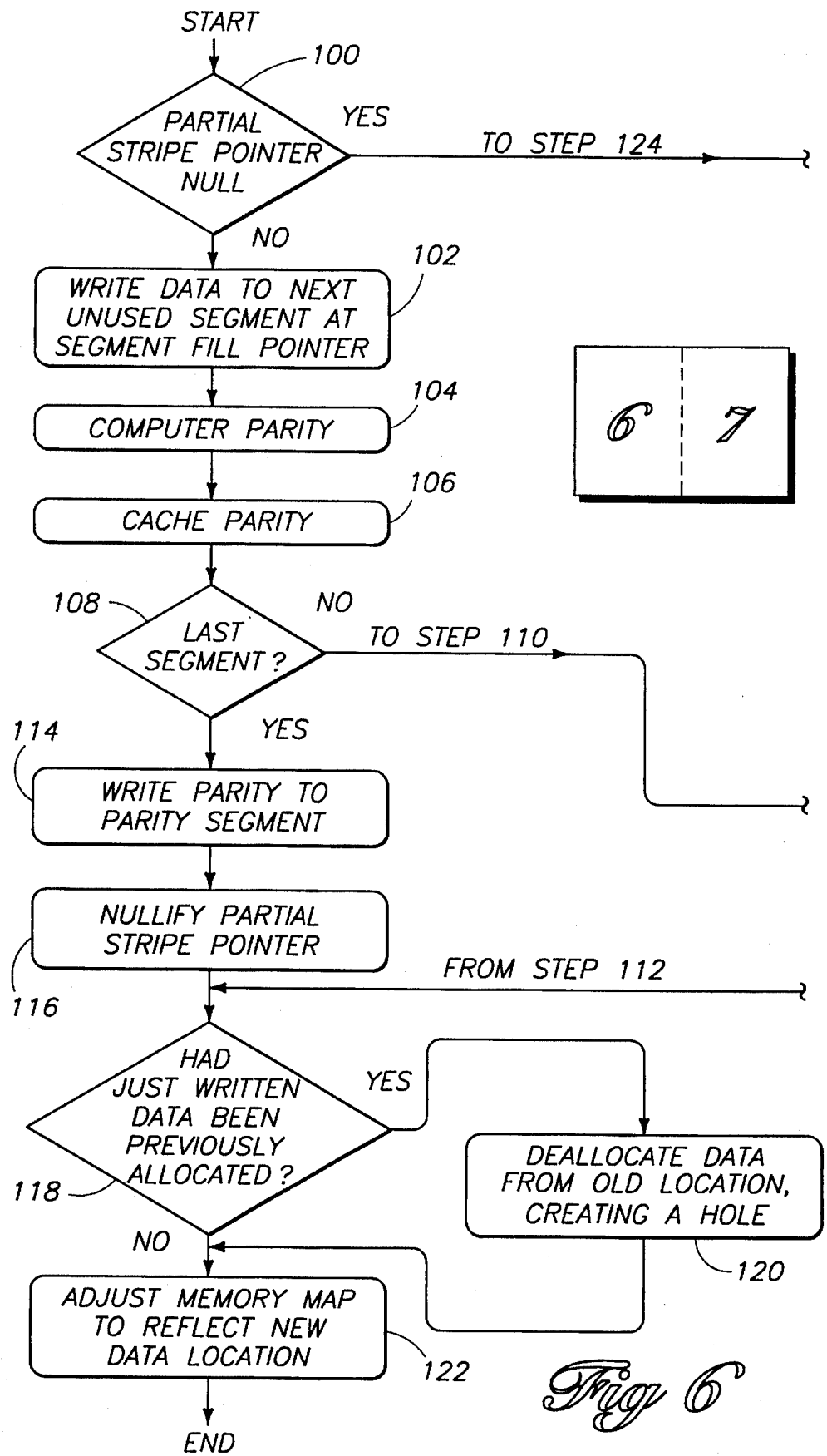
FIGS. 6 and 7 present a flow diagram of preferred steps for writing data to the disk array according to parity redundancy techniques.
Figure 7:
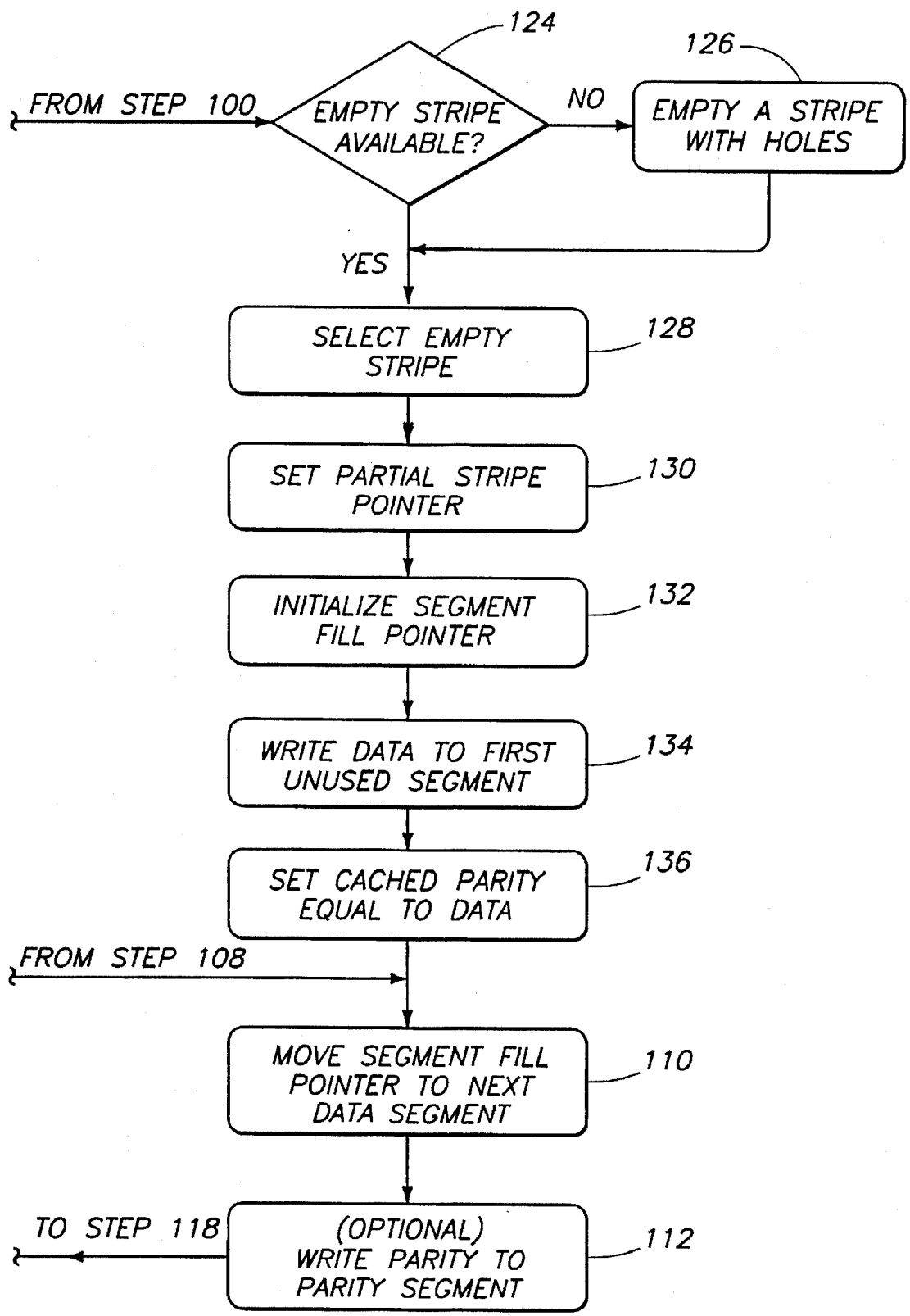

FIGS. 6 and 7 illustrate a preferred method for writing user data to a disk array according to parity redundancy techniques. The process begins at step 100 (FIG. 6) where it is determined whether the partial stripe pointer 62 is null, meaning that it is not presently referencing a non-filled stripe. If the partial stripe pointer is pointing to a stripe (i.e., the "no" branch from step 100), user data is written to the next unused segment referenced by the segment fill pointer 64 (step 102). An incremental parity value for all user data contained those segments that have been filled is computed by XORing the new user data into the cached parity (step 104) and re-cached (step 106).

At step 108, it is determined whether the segment fill pointer 64 is referencing the last segment in the stripe. The RAID management system tracks the allocation of new space in a stripe. It knows how many segments are in a stripe, and all unused segments that have not yet been allocated in the stripe. As discussed above, the RAID management system further assumes that all segments in front of the segment fill pointer are represented in the stripe parity and all segments in back of the pointer are empty and not accounted for in the stripe parity. Additionally, the RAID management system assumes that non-referenced stripes which contain data have all segments incorporated into their stripe parity and all empty non-referenced stripes have segments that are not part of any parity.

As a result of these operating parameters, the RAID management system knows the parity status of any segment in the disk array as well as the location of the pointers in the array. The RAID management system therefore knows whether or not the segment fill pointer has reached the end of the stripe. If the pointer has not yet reached the last segment (i.e., the "no" branch from step 108), the segment fill pointer is moved to the next data segment (step 110, FIG. 7). The parity value computed at step 104 can then be optionally written to the parity segment in the stripe (step 112).

With reference again to FIG. 6, if the segment fill pointer has reached the last segment, the cached parity value which represents parity for the entire stripe is written to the parity segment in the stripe (step 114). At this point, the stripe is completely filled with user data and redundant information. Accordingly, the partial stripe pointer can be nullified until used again to identify the next empty stripe (step 116), as described below in more detail.

At step 118, the RAID management system evaluates whether the user data that was just written to the segments in the stripe had been previously allocated any where else on the disk array. Such a situation arises when, for example, the RAID management system is reorganizing user data on the disk array and moves user data from one location to another. If it is rewritten user data (i.e., the "yes" branch from step 118), the RAID management system deallocates the user data from its old location, thereby creating a "hole" (i.e., an empty segment) in the previous stripe (step 120). At step 122, the memory map 60 is updated to reflect the new data location.

With reference again to initial step 100, the partial stripe pointer is null during the interlude between completion of one stripe and the identification of a new empty strip. If the partial stripe pointer is null (i.e., the "yes" branch from step 100), the RAID management system searches for a new empty stripe (step 124, FIG. 7). In the event that an empty stripe cannot be identified (i.e., the "no" branch from step 124), the RAID management system finds a partially filled stripe having "holes" therein and empties it (step 126). This process is known as "garbage collection" and an example is shown in FIG. 8.

Figure 8:
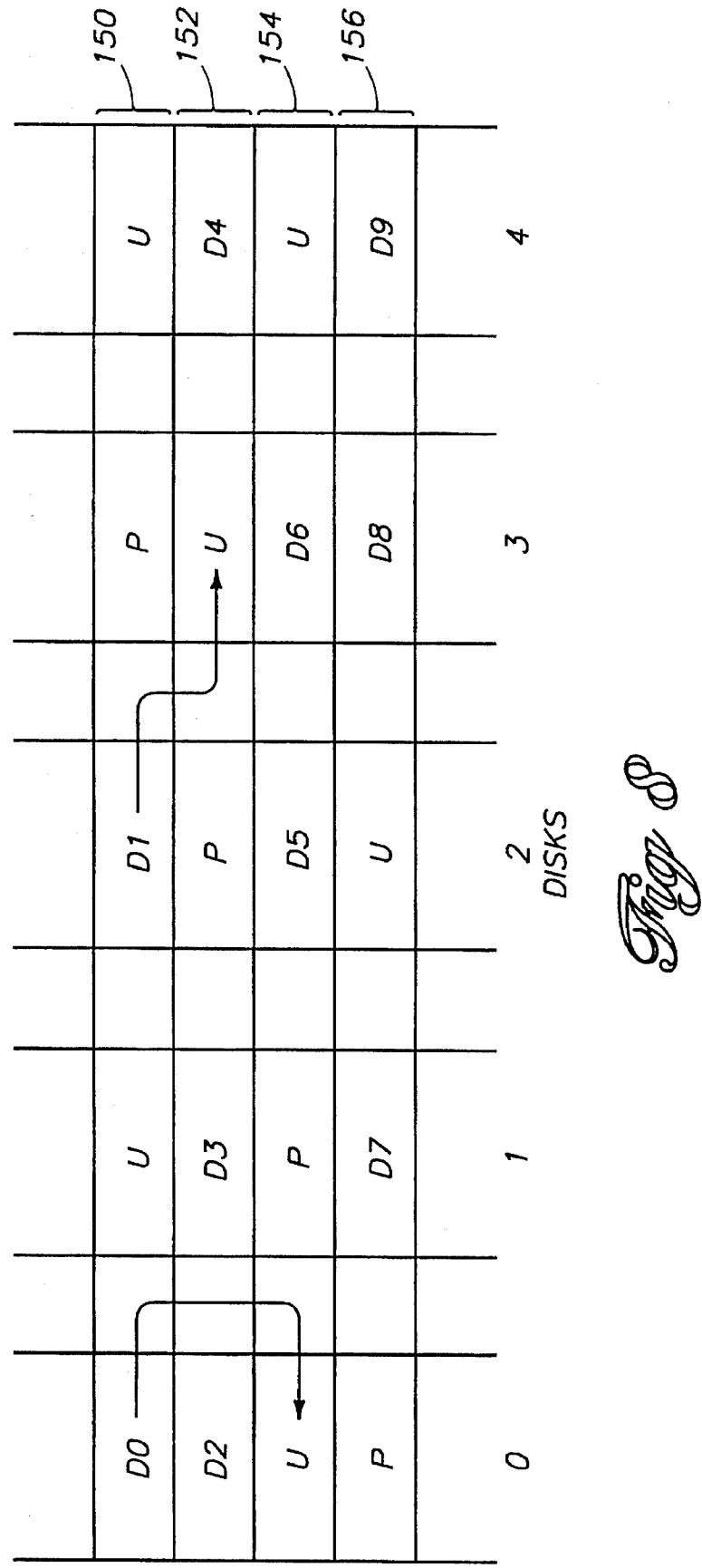
FIG. 8 is a diagrammatic illustration of storage space on multiple storage disks and demonstrates a garbage collection technique.

FIG. 8 shows stripes 150–156 traversing across disks 0–4 of the disk array. The segments containing user data are designated by the letter "D" followed by a number. Empty or unused segments are designated by the letter "U". Notice that unused segments U create "holes" in the stripes 150–156. For example purposes, suppose that the RAID management system decides to empty stripe 150. User data D0 in the segment on disk 0 is moved to an unused segment in stripe 154, and user data D1 in the segment on disk 2 is moved to an unused segment in stripe 152. This data movement empties stripe 150, which now consists of unused data segments and a parity segment. At the same time, the data movement fills the "holes" in other stripes, making those stripes more full.

This example type of the garbage collection process randomly moves user data from the stripe to be emptied to holes in other stripes. In another implementation, the garbage collection process sequentially writes user data from the designated stripe to a new empty stripe in the same manner described above for writing user data sequentially by segment. Other garbage collection techniques may likewise be used to empty stripes per step 126 of FIG. 7.

With reference again to FIG. 7, the RAID management system selects the empty stripe (step 128) and sets the partial stripe pointer to reference the stripe (step 130). The segment fill pointer is initialized to reference the beginning of the stripe (step 132). User data is then written to the first unused segment (step 134). At step 136, the initial parity value is set equal to the user data and cached. Thereafter, the segment fill pointer is moved to the next data segment (step 110) and the process is continued for the remaining segments of the stripe.

The implementation described above employs two types of pointers which identify empty stripes and segments within these stripes. In another embodiment, multiple pairs of pointers may be retained in NVRAM, such as one pair per RAID area. The management of cached parity is coordinated with the incremental filling of multiple stripes. If multiple pairs of pointers are used, coordination may involve caching multiple parity segments from different stripes and/or posting the cache parity in a pattern that allows timely reuse of cache resources, such as posting parity after each data segment is written.

In another optional implementation, the RAID management system can be configured to select partially filled stripes that contain user data in one or more contiguous segments at the beginning of the stripe, while the segments at the end of the stripe are empty. The RAID management system initializes the segment fill pointer to the first empty segment in the partially filled stripe and then continues the sequential write according to the same techniques described above. It is further noted that the process can be continued stripe by stripe to write entire RAID areas.

In another preferred implementation, each pair of pointers is combined into a single pointer which identifies both a stripe and a segment therein.

As an alternative embodiment to using two types of pointers, the RAID management system can employ a bit map as its means for determining which data segments are incorporated into a stripe parity and which are not. The bit map would contain information on every single segment in the disk array. This embodiment requires more memory space in the NVRAM, as compared to the pointers, but is effective for tracking the parity of the data segments.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A method for writing user data to a disk array according to redundant parity storage techniques, the disk array having multiple storage disks and being configured into multiple stripes where each stripe extends across multiple ones of the storage disks, each stripe comprising multiple segments of storage space where each segment is a portion of the stripe that resides on a single storage disk in the disk array, the method comprising the following steps:

(a) differentiating between segments which hold user data or parity information and segments which are empty;

(b) identifying a non-filled stripe in the disk array, the non-filled stripe having multiple empty segments;

(c) locating one of the empty segments in the identified non-filled stripe;

(d) writing user data to the one empty segment in the stripe without writing user data to other empty segments in the non-filled stripe;

(e) determining, after the user data is written to the one empty segment per step (d), a parity value for the user data contained in those segments in the non-filled stripe that have been written to; and (f) repeating steps (c)–(e) to fill one or more of the other empty segments in the non-filled stripe.

2. A method according to claim 1 wherein the identifying step comprises using a partial stripe pointer to reference the non-filled stripe.

3. A method according to claim 1 wherein the locating step comprises using a segment fill pointer to reference a segment to be written to in the stripe.

4. A method according to claim 1 wherein:

the identifying step comprises using a partial stripe pointer to reference the non-filled stripe;

the locating step comprises using a segment fill pointer to reference a segment to be written to in the stripe;

the method further comprising:
    providing a non-volatile memory separate from the disk array; and
    storing the partial stripe pointer and the segment fill pointer in the non-volatile memory.

5. A method according to claim 1 wherein the locating step comprises sequentially referencing the empty segments contiguously according to their order within the non-filled stripe.

6. A method according to claim 1 wherein the step of determining parity comprises computing a parity value based on a logical function of the user data contained in the segments in the non-filled stripe that have been written to.

7. A method according to claim 1 further comprising the following additional steps:

providing a non-volatile memory separate from the disk array; and temporarily caching the parity value after each said determining step (e) in the non-volatile memory.

8. A method according to claim 1 further comprising the following additional steps:

temporarily caching the parity value after each said determining step (e); and the step of determining parity comprises computing a new parity value based on a logical function of the previously cached parity value and user data most recently written into an empty segment in the stripe.

9. A method according to claim 1 further comprising the step of writing the parity value to the disk array after each said determining step (e).

10. A method according to claim 1 further comprising the following additional steps:

writing the parity value to the disk array after each said determining step (e); and the step of determining parity comprises reading the previously written parity value from the disk array and computing a new parity value based on a logical function of the previously written parity value and user data most recently written into an empty segment in the stripe.

11. A method according to claim 1 wherein the identifying step comprises identifying an entirely empty stripe, the method further comprising:

in the event that an empty stripe cannot be identified, identifying a partially filled stripe having both empty and filled segments and emptying the partially filled stripe by moving user data from the filled segments to other locations on the disk array.

12. A method for writing user data to a disk array according to redundant parity storage techniques, the disk array having multiple storage disks and being configured into multiple stripes where each stripe extends across multiple ones of the storage disks, each stripe comprising multiple segments of storage space where each segment is a portion of the stripe that resides on a single storage disk in the disk array, the method comprising the following steps:

(a) providing a non-volatile memory separate from the disk array;

(b) providing a partial stripe pointer in the non-volatile memory that references individual stripes in the disk array;

(c) providing a segment fill pointer in the non-volatile memory that references individual segments in the referenced stripe;

(d) selecting an empty stripe by setting the partial stripe pointer to that empty stripe;

(e) selecting a first segment in the selected stripe by setting the segment fill pointer to that first segment;

(f) writing user data to the first segment while leaving empty other segments in the stripe;

(g) computing a parity value for only the first segment in the stripe;

(h) caching the parity value in the non-volatile memory;

(i) selecting a next segment in the stripe using the segment fill pointer;

(j) writing user data to the next segment in the stripe; and (k) computing another parity value based on the cached parity value and the user data written to the next segment.

13. A method according to claim 12 further comprising the step of repeating steps (i)–(k) until all segments in the stripe that are used to store user data are filled.

14. A method according to claim 13 further comprising the step of writing a last computed parity value from the non-volatile memory to a segment in the stripe on the disk array.

15. A data storage system comprising:

a disk array having multiple storage disks, the disk array being configured into multiple stripes where each stripe extends across multiple ones of the storage disks, each stripe comprising multiple segments of storage space where each segment is a portion of the stripe that resides on a single storage disk in the disk array;

a disk array controller coupled to the disk array to coordinate data transfer to and from the storage disks;

a memory manager operatively coupled to the disk array controller to manage memory allocation for storing user data redundantly according to parity redundancy techniques, the memory manager placing user data in data segments and parity information in parity segments whereby at least one parity segment and one or more data segments are included in each stripe, the memory manager having means for determining which data segments are incorporated into the parity information of the stripe;

the memory manager selecting a non-filled stripe and an empty segment in that stripe; and the memory manager writing user data to the selected segment and incrementally determining a parity value for the stripe after each segment is written to, the parity value being based upon the user data contained in those segments of the stripe that have been written to.

16. A data storage system according to claim 15 wherein the determining means of the memory manager comprises:

a partial stripe pointer to reference individual stripes in the disk array;

a segment fill pointer to reference individual segments in the referenced stripe; and the memory manager using the pointers to select a non-filled stripe and a segment in that stripe.

17. A data storage system according to claim 16 further comprising a non-volatile memory to store the partial stripe pointer and the segment fill pointer, the non-volatile memory also caching the parity value.

18. A data storage system according to claim 15 wherein:

the disk array is configured to group the multiple stripes into a plurality of RAID areas where each RAID area contains more than one stripe;

the determining means of the memory manager comprises multiple pairs of partial stripe pointers and segment fill pointers in which one pair corresponds to each RAID area, each pair having a partial stripe pointer to reference an individual stripe in the corresponding RAID area and a segment fill pointer to reference an individual segment within the stripe referenced by the partial stripe pointer.

19. A data storage system according to claim 15 further comprising:

a non-volatile memory resident to cache the parity value each time the parity value is determined; and the memory manager computing a new parity value based on a logical function of the previously cached parity value and user data most recently written into an empty segment in the stripe.

20. A data storage system according to claim 15 wherein the memory manager writes the parity value to a segment in the stripe of the disk array after all segments in the stripe that have been used to store user data have been filled.

21. A data storage system according to claim 15 wherein:

the memory manager writes the parity value to a segment in the stripe of the disk array each time the parity value is determined; and the memory manager reads the previously written parity value from the disk array and computes a new parity value based on a logical function of the previously written parity value and user data most recently written into an empty segment in the stripe.

* * * * *